Figure 1:
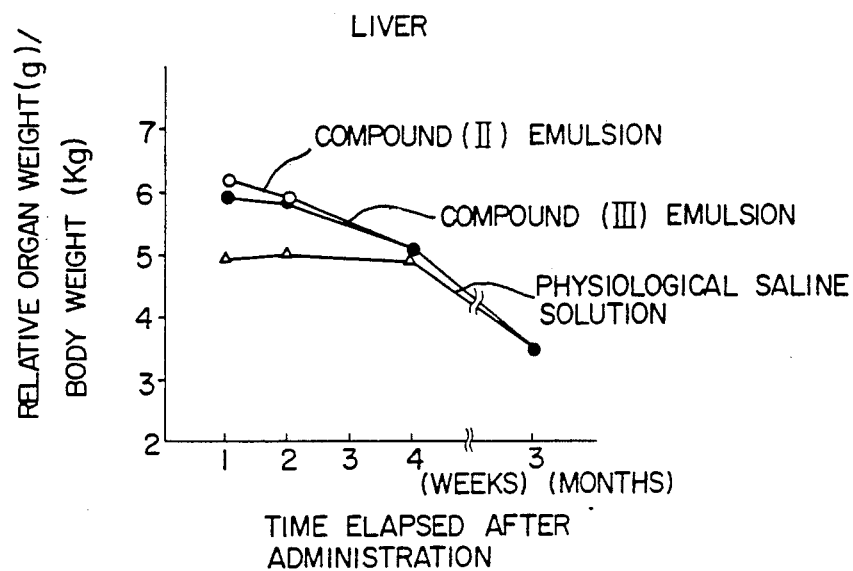

United States Patent [19]

Yokoyama et al.

[11] Patent Number: 4,713,459

[45] Date of Patent: Dec. 15, 1987

[54] PERFLUORO COMPOUNDS

[75] Inventors: Kazumasa Yokoyama, Toyonaka; Chikara Fukaya, Osaka; Yoshio Tsuda, Takarazuka; Taizo Ono, Osaka; Yoshio Arakawa, Suita; Tadakazu Suyama, Kyoto, all of Japan

[73] Assignee: The Green Cross Corporation, Osaka, Japan

[21] Appl. No.: 830,094

[22] Filed: Feb. 18, 1986

Related U.S. Application Data

[62] Division of Ser. No. 442,416, Nov. 17, 1982, Pat. No. 4,591,593.

[30] Foreign Application Priority Data

Nov. 27, 1981 [JP] Japan .................. 56-191357
Jun. 25, 1982 [JP] Japan .................. 57-110200

[51] Int. Cl.$^4$ ............ A61K 31/47; A61K 31/40; C07D 209/10; C07D 217/22
[52] U.S. Cl. ............ 546/150; 546/164; 548/452; 548/469; 548/470; 548/515
[58] Field of Search .......... 546/150, 164; 548/470, 548/469

[56] References Cited

U.S. PATENT DOCUMENTS

| | | | |
|---|---|---|---|
| 3,823,091 | 7/1974 | Samejima et al. | 514/723 |
| 3,911,138 | 10/1975 | Clark | 514/746 |
| 3,962,439 | 6/1976 | Yokoyama et al. | 514/227 |
| 4,252,827 | 2/1981 | Yokoyama et al. | 514/776 |
| 4,591,593 | 5/1986 | Yokoyama et al. | 546/150 |

OTHER PUBLICATIONS

Yokoyama, et al., "Chemical Abstracts", vol. 99, 1983, col. 99:11555w.
Yokoyama, et al., "Chemical Abstracts", vol. 100, 1984, col. 100:22586f.

Primary Examiner—Glennon H. Hollrah
Assistant Examiner—James H. Turnipseed
Attorney, Agent, or Firm—Cushman, Darby & Cushman

[57] ABSTRACT

A novel compound of the formula,

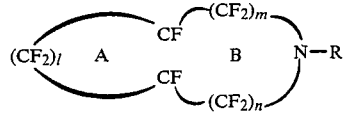

wherein R denotes a lower perfluoroalkyl group, l is an integer of 3 or 4, n+m is an integer of 2 or 3, provided that n may be zero, and at least one of ring A and ring B may be substituted by a lower perfluoroalkyl group, prepared by reacting the corresponding perhydro compound with fluorine is useful as a material capable of carrying oxygen in an aqueous emulsion for lifesaving a patient suffering from massive hemorrhage and for preserving internal organs in transplantation.

11 Claims, 2 Drawing Figures

PERFLUORO COMPOUNDS

This is a division of application Ser. No. 442,416, filed Nov. 17, 1982 now U.S. Pat. No. 4,591,593.

This invention relates to a novel perfluoro compound.

More particularly, this invention relates to a perfluoro compound represented by the formula

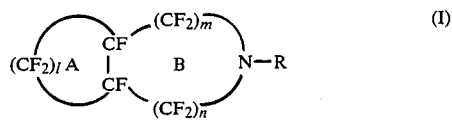

wherein R denotes a lower perfluoroalkyl group, l is an integer of 3 or 4, m+n is an integer of 2 or 3, provided that n may be zero, and at least one of ring A and ring B may be substituted by a lower perfluoroalkyl group.

In the general formula (I) given above, since l denotes an integer of 3 or 4, and m+n denotes 2 or 3, the ring A and the ring B each represents a five-membered or a six-membered ring, and together form a condensed ring.

As the condensed ring formed by the ring A and B, there can be cited perhydro-quinoline, -isoquinoline, -indole, -isoindole, -cyclopenta[b]pyrrole, -cyclopenta[c]pyrrole, -pyridine, -isopyridine or the like, all of which have been perfluorinated.

In the general formula (I), the lower perfluoroalkyl group denoted by R may be either of straight chain or of branched chain. Examples thereof include those having 1–4 carbon atoms, such as perfluoromethyl group, perfluoroethyl group, perfluoro-n-propyl group, perfluoro-isopropyl group, perfluoro-n-butyl group, perfluoro-isobutyl group, perfluoro-sec-butyl group or perfluoro-tert-butyl group.

The ring A and/or the ring B may be substituted at any position thereof by one or more than one (preferably one or two) lower perfluoroalkyl group(s) in addition to the above-mentioned substituent denoted by R. Examples of the lower perfluoroalkyl group suitable as such as substituent are similar to those which were described above referring to R. In case where two or more of said substituents are present, they may be different from each other.

The compound of the formula (I) according to the present invention can be prepared by fluorinating a corresponding known perhydro compound. The methods of fluorination include, for example, direct fluorination, fluorination by use of cobalt fluoride, and electrolytic fluorination.

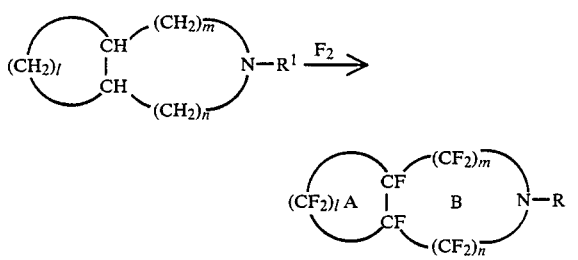

R' is a lower alkyl group.

The preparation of the compound represented by the formula (I) according to this invention is preferably performed by the electrolytic fluorination method. This is performed, for example, by mixing anhydrous hydrogen fluoride and a perhydro compound used as the starting compound in an electrolytic cell and, after dissolving the mixture, subjecting the resulting solution to electrolysis. The voltage, the current density at the anode, and the temperature of electrolytic solution in said electrolysis are 3–9 V, 1–300 A/dcm$^2$, and 4°–10° C., respectively.

The compound of formula (I) thus formed precipitates in the lower layer of the electrolytic cell, being insoluble in anhydrous hydrofluoric acid. The isolation and purification of the compound from the precipitate are carried out, for example, adding a mixture of equal volumes of an aqueous solution of alkali and an amine compound to the recovered precipitate, refluxing, then separating the lowermost layer containing the objective compound of formula I (the partially fluorinated compounds going into the amine layer in this separation), washing the former layer with an aqueous acetone solution containing suitable amount of potassium iodide to remove compounds having a fluorine atom bonded to the nitrogen atom, and by subsequent fractional distillation to obtain the fraction of the objective compound.

According to the present invention, there is also provided an emulsion of the perfluoro compound of the formula (I).

Since the compound of the formula (I) of this invention is capable of dissolving a large amount of oxygen, metabolically inert, and can be excreted rapidly from the body, it is useful to be used as a perfluorocarbon compound emulsion for clinical purpose which is capable of carrying oxygen and can be used for saving the life of a patient suffering from massive hemorrahgeing and for preserving internal organs in transplantation.

It has been already reported that the perfluorocarbon compound emulsion may possibly be used as a red cells substitute for mammals and as a perfusion fluid for preservation of internal organs to be transplanted, particularly as a substitute infusion fluid capable of transporting oxygen. There are reported, for example, perfluoro cyclic carbon compounds, such as perfluoromethylcyclohexane, perfluoro-1,3-dimethylcyclohexane, perfluorodecalin and perfluoromethyldecalin (U.S. Pat. No. 3,911,138 and U.S. Pat. No. 3,962,439), perfluoro tert-alkylamines (U.S. Pat. No. 3,823,091), perfluoro alkyltetrahydropyrans, perfluoro alkyltetrahydrofurans, perfluoro N-alkylpyridines, and perfluoro N-alkylmorpholines or mixtures thereof (U.S. Pat. No. 4,252,827).

There are, however, disclosed no such perfluoro(-heterocyclic amines) having a condensed ring structure as shown in Formula (I).

The perfluoro compounds of the present invention can be used alone or in mixture as oxygen transporting material in an emulsion thereof. Those having 8 to 12 carbon atoms, and preferably 9 to 11 carbon atoms are preferable for the purpose, and in some cases the lower perfluoroalkyls denoted by R in Formula (I) may preferably have 1 or 2 carbon atoms. Also, the rings A and B in the formula may be either substituted or unsubstituted by a lower perfluoroalkyl, and if substituted, they may preferably have a perfluoroalkyl of 1 or 2 carbon atoms.

The preferred perfluoro compounds of the present invention are shown as the objective compounds in Compound Preparation Examples 1 to 97.

In fluorocarbon compound emulsions, the size of particle plays an important role in the toxicity and efficacy of the emulsion [K. Yokoyama, K. Yamanouchi, M. Watanabe, R. Murashima, T. Matsumoto, T. Hamano, H. Okamoto, T. Suyama, R. Watanabe, and R. Naitoh: Preparation of perfluorodecalin emulsion, an approach to the red cells substitute, Federation Proceeding, 34,1478-1483 (May, 1975)]. An emulsion of larger particle size is more toxic and shorter in retention time of the particles in the blood stream. Accordingly, when the fluorocarbon compound emulsion is intended for use as an artificial blood substitute for saving the life of a patient suffering from massive hemorrhageing, its average particle size should be $0.3\mu$ or less in diameter, preferably $0.2\mu$ or less (U.S. Pat. No. 3,958,014).

In addition to having the desired particle size, it is necessary, in order that the fluorocarbon compound emulsion may be used as a blood substitute, that after completing its original role of transporting oxygen, the intravenously administered fluorocarbon compound must be excreted from the body as rapidly as possible. Moreover, the emulsion should be stable to thermal sterilization and in storage for a long period of time. Also, the emulsion should allow the addition thereto of a plasma expander such as hydroxyethyl-starch (HES) and dextran.

The perfluoro compound of the present invention satisfies all of the above-mentioned requirements.

The attached drawings show the changes of the amounts of perfluoro compound accumulated in internal organs with time after the perfluoro compound emulsions of this invention have been administered to animals.

Figure 2:
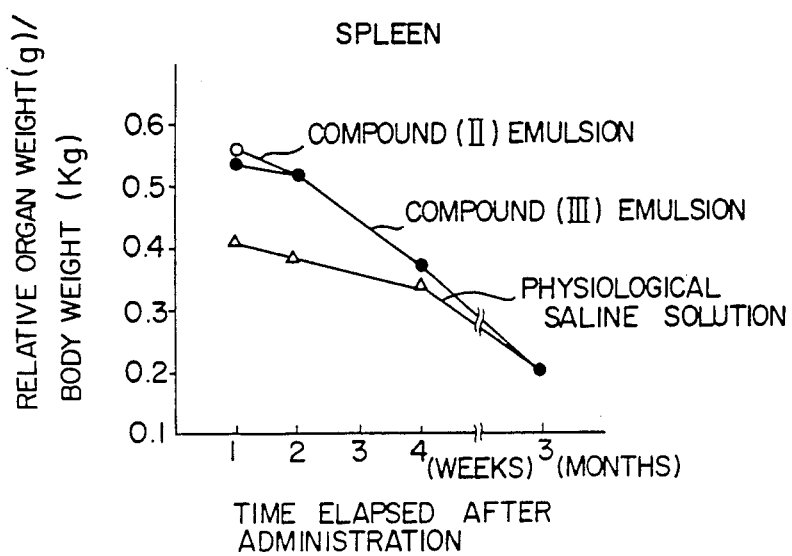

FIG. 1 shows the above-mentioned change with time in the liver of wister strain rat, and FIG. 2 shows that in the spleen.

The present emulsion is an oil-in-water type emulsion containing perfluoro compounds dispersed in water. The proportion of perfluoro compounds in the emulsion is 5–50% (W/V), preferably 10–40% (W/V).

The symbol "% (W/V) referred to in the specification and claim of this application means the amount proportion of a material by weight (gram) based on 100 ml of the resulting emulsion.

The preparation of the emulsion can be carried out in any known method so long as the above-mentioned requirements are satisfied. But a method using high pressure injection is preferably employed wherein, according to the method described in U.S. Pat. No. 4,252,827 for example, high-molecular-weight nonionic surface active agent is used as emulsifier, and phospholipid and fatty acid are used as emulsifying adjuvant.

The high-molecular-weight nonionic surface active agent suitable for the present emulsion has a molecular weight of 2,000 to 20,000 and includes, for example, polyoxyethylene-polyoxypropylene copolymers, polyoxyethylene fatty acid esters and polyoxyethylene-castor oil derivatives. The amount to be used based on the emulsion is 1–5% (W/V). Examples of phospholipids include egg yolk phospholipid and soy bean phospholipid, the amount to be used being 0.1–1.0% (W/V). If desired, there may be further added as an emulsifier adjuvant, for example, a fatty acid having 8–22, preferably 14–20 carbon atoms and a physiologically acceptable salt, e.g. alkali metal salt, such as sodium or potassium salt, or a monoglyceride thereof, which includes, for example, caprylic acid, capric acid, lauric acid, myristic acid, palmitic acid, stearic acid, behenic acid, palmitoleic acid, linoleic acid, arachidonic acid and sodium or potassium salt and monoglyceride thereof. The amount thereof to be used is 0.001–0.01% (W/V).

As the medium for the present emulsion, a physiologically acceptable aqueous solution, such as physiological saline solution or lactated Ringer's solution, may be employed. If necessary, there may be added thereto an agent for achieving the desired isotonicity, such as glycerol, and a plasma expander for regulating the osmotic pressure of colloidal solution, such as HES or dextran.

The emulsion of the present invention can be prepared by mixing the above-mentioned ingredients in any order to obtain a crude emulsion, and then homogenizing the crude emulsion by means of a suitable high-pressure jet type emulsifier, e.g. Manton-Gaulin type homogenizer, until the particle diameters become less than $0.3\mu$.

When the perfluoro compound emulsion of this invention is used, for example, as the infusion fluid for transporting oxygen, it is usually administered by intravenous infusion. The amount to be administered is 50–200 cc per one time for an adult.

The present invention is further illustrated in detail by the following Examples and Experimental Examples, which should not be construed to limit the invention thereto.

COMPOUND PREPARATION EXAMPLE 1

Into an electrolylic cell made of Monel metal with an inner volume of 1.5 l, which is provided with electrode plates (six plates as anode and seven plates as cathode) made of nickel (purity: 99.6% or higher) arranged alternately with an inter-electrode distance of 1.7–2.0 mm, the effective anode surface area being 10.5 dm$^2$, and with a reflux condenser made of copper at the upper part of the cell, was introduced 1.2 l of hydrogen fluoride, and trace amounts of impurities present in the system (moisture and sulfuric acid) were removed by preliminary electrolysis. Then, 0.85 mol (130 g) of N-methyl-perhydroquinoline was dissolved into the hydrogen fluoride, and electrolysis was carried out, while introducing helium gas from the bottom of the cell at a rate of 100 ml/min., under the conditions of anode current density of 1.0–2.0 A/dm$^2$, voltage of 4.0–6.2 V and solution temperature of 4°–10° C., until the electrolytic voltage had reached 9.0 V. The ampere-hours amounted to 1051. Hydrogen fluoride was added at a rate of 200 ml per 24 hours during the electrolysis. The gas evolved during the electrolysis was first passed through an iron pipe filled with sodium fluoride pellets to remove the accompanying hydrogen fluoride, and then led through a trap cooled with dry ice-aceton mixture to be collected by liquefaction. There was obtained 9.5 g of a colorless liquid. The electrolytic solution in the cell separated into two layers, the upper layer being hydrogen fluoride and the lower layer being fluorocarbons. After separation, the lower layer weighed 263 g.

The above-mentioned liquid collected by cooling of the evolved gas and the lower layer liquid from electrolytic cell were combined, equal volumes of 70% aqueous potassium hydroxide solution and diisobutylamine were added thereto, and the resulting mixture was refluxed for seven days. The perfluoro compounds layer was separated in a separatory funnel, washed with 90% (W/V) of aqueous acetone solution containing 10% (W/V) potassium iodide, and then subjected to precise fractional distillation on a precise fractional distillation apparatus equipped with a spinning band column to obtain 44 g of perfluoro-N-methylperhydroquinoline. Yields: 10%. B.P.: 150°–155° C./760 mmHg. This compound was analyzed by infrared absorption spectroscopy, F-nuclear magnetic resonance spectroscopy and mass spectroscopy, and was confirmed to be the objective compound, that is, perfluoro-N-methyldecahydroquinoline having the structure of the following formula:

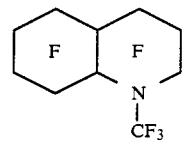

COMPOUND PREPARATION EXAMPLES 2–97

In a similar manner to that described in Compound Preparation Example 1 and using the perhydro compounds listed in Table 1 as starting material, corresponding perfluoro compounds were obtained. The results were shown in Table 1.

TABLE 1

| Example No. | Starting material | Perfluoro compound | B.P. (°C./760 mmHg) |
|---|---|---|---|
| 2 | N—methylperhydroisoquinoline | (structure) | 151–155° C. |
| 3 | N—methylperhydroindole | (structure) | 122–126° C. |
| 4 | N—methylperhydroisoindole | (structure) | 124–125° C. |
| 5 | N—methylperhydropyridine | (structure) | 121–127° C. |
| 6 | 2-Methyl-N—methylperhydroindole | (structure) | 145–155° C. |
| 7 | 3-Methyl-N—methylperhydroindole | (structure) | 144–154° C. |
| 8 | 3a-Methyl-N—methylperhydroindole | (structure) | 145–156° C. |
| 9 | 7-Methyl-N—methylperhydroindole | (structure) | 145–155° C. |

TABLE 1-continued

| Example No. | Starting material | Perfluoro compound | B.P. (°C./760 mmHg) |
|---|---|---|---|
| 10 | 6-Methyl-N—methylperhydroindole | (structure: bicyclic with CF₃, F, F, N—CF₃) | 145–155° C. |
| 11 | 5-Methyl-N—methylperhydroindole | (structure: bicyclic with CF₃, F, F, N—CF₃) | 145–155° C. |
| 12 | 4-Methyl-N—methylperhydroindole | (structure: bicyclic with CF₃, F, F, N—CF₃) | 145–155° C. |
| 13 | 1-Methyl-N—methylperhydroindole | (structure: bicyclic with CF₃, F, F, N—CF₃) | 145–155° C. |
| 14 | 3a-Methyl-N—methylperhydroisoindole | (structure: bicyclic with CF₃, F, F, N—CF₃) | 144–154° C. |
| 15 | 4-Methyl-N—methylperhydroisoindole | (structure: bicyclic with CF₃, F, F, N—CF₃) | 146–156° C. |
| 16 | 5-Methyl-N—methylperhydroisoindole | (structure: bicyclic with CF₃, F, F, N—CF₃) | 145–155° C. |
| 17 | 1,7-Dimethylperhydropyrindine | (structure: bicyclic with F, F, CF₃, N—CF₃) | 146–156° C. |
| 18 | 1,7a-Dimethylperhydropyridine | (structure: bicyclic with F, F, CF₃, N—CF₃) | 146–156° C. |

TABLE 1-continued

| Example No. | Starting material | Perfluoro compound | B.P. (°C./760 mmHg) |
|---|---|---|---|
| 19 | 1,2-Dimethylperhydropyridine | (bicyclic perfluoro structure with N—CF$_3$ and CF$_3$ substituent) | 146–156° C. |
| 20 | 1,3-Dimethylperhydropyridine | (bicyclic perfluoro structure with N—CF$_3$ and CF$_3$ substituent) | 146–155° C. |
| 21 | 1,4-Dimethylperhydropyridine | (bicyclic perfluoro structure with N—CF$_3$ and CF$_3$ substituent) | 146–155° C. |
| 22 | 1,5-Dimethylperhydropyridine | (bicyclic perfluoro structure with N—CF$_3$ and CF$_3$ substituent) | 146–155° C. |
| 23 | 1,6-Dimethylperhydropyridine | (bicyclic perfluoro structure with N—CF$_3$ and CF$_3$ substituent) | 146–156° C. |
| 24 | N—Ethylperhydroisoindole | (bicyclic perfluoro structure with N—CF$_2$CF$_3$) | 144–152° C. |
| 25 | N—Methylperhydroisopyridine | (bicyclic perfluoro structure with N—CF$_3$) | 125–135° C. |
| 26 | 1,2-Dimethylperhydroisopyridine | (bicyclic perfluoro structure with N—CF$_3$ and CF$_3$ substituent) | 145–155° C. |
| 27 | 2,3-Dimethylperhydroisopyridine | (bicyclic perfluoro structure with N—CF$_3$ and CF$_3$ substituent) | 144–155° C. |
| 28 | 2,4-Dimethylperhydroisopyridine | (bicyclic perfluoro structure with N—CF$_3$ and CF$_3$ substituent) | 144–156° C. |

TABLE 1-continued

| Example No. | Starting material | Perfluoro compound | B.P. (°C./760 mmHg) |
|---|---|---|---|
| 29 | 2,4a-Dimethylperhydroisopyridine | (structure with CF₃ at 4a, F,F, N-CF₃) | 144–155° C. |
| 30 | 2,5-Dimethylperhydroisopyridine | (structure with CF₃, F, F, N-CF₃) | 144–155° C. |
| 31 | 2,6-Dimethylperhydroisopyridine | (structure with CF₃, F, F, N-CF₃) | 145–155° C. |
| 32 | 2,7-Dimethylperhydroisopyridine | (structure with F, F, N-CF₃, CF₃) | 144–155° C. |
| 33 | 2,7a-Dimethylperhydroisopyridine | (structure with F, F, CF₃ at 7a, N-CF₃) | 145–156° C. |
| 34 | 2-Ethyl-1-methyl-perhydrocyclopenta[b]pyrrole | (structure with F, F, CF₂CF₃, N-CF₃) | 145–155° C. |
| 35 | 3-Ethyl-1-methylperhydrocyclopenta[b]pyrrole | (structure with CF₂CF₃, F, F, N-CF₃) | 145–155° C. |
| 36 | 3a-Ethyl-1-methylperhydrocyclopenta[b]pyrrole | (structure with CF₂CF₃, F, F, N-CF₃) | 145–155° C. |
| 37 | 4-Ethyl-1-methylperhydrocyclopenta[b]pyrrole | (structure with CF₂CF₃, F, F, N-CF₃) | 145–155° C. |
| 38 | 5-Ethyl-1-methylperhydrocyclopenta[b]pyrrole | (structure with F, CF₂CF₃, F, N-CF₃) | 145–155° C. |
| 39 | 6-Ethyl-1-methylperhydrocyclopenta[b]pyrrole | (structure with F, F, CF₂CF₃, N-CF₃) | 145–155° C. |

TABLE 1-continued

| Example No. | Starting material | Perfluoro compound | B.P. (°C./760 mmHg) |
|---|---|---|---|
| 40 | 6a-Ethyl-1-methylperhydrocyclopenta[b]pyrrole | (structure with CF₂CF₃, CF₃, F, N–CF₃) | 145–155° C. |
| 41 | 1,2,3-Trimethylperhydrocyclopenta[b]pyrrole | (structure with CF₃ groups, F, N–CF₃) | 144–156° C. |
| 42 | 1,2,3a-Trimethylperhydrocyclopenta[b]pyrrole | (structure with CF₃, F, N–CF₃) | 145–155° C. |
| 43 | 1,2,4-Trimethylperhydrocyclopenta[b]pyrrole | (structure with CF₃, F, N–CF₃) | 144–155° C. |
| 44 | 1,2,5-Trimethylperhydrocyclopenta[b]pyrrole | (structure with CF₃, F, N–CF₃) | 145–155° C. |
| 45 | 1,2,6-Trimethylperhydrocyclopenta[b]pyrrole | (structure with CF₃, F, N–CF₃) | 144–155° C. |
| 46 | 1,2,6a-Trimethylperhydrocyclopenta[b]pyrrole | (structure with CF₃, F, N–CF₃) | 145–156° C. |
| 47 | 1,3,3a-Trimethylperhydrocyclopenta[b]pyrrole | (structure with CF₃, F, N–CF₃) | 145–156° C. |
| 48 | 1,3,4-Trimethylperhydrocyclopenta[b]pyrrole | (structure with CF₃, F, N–CF₃) | 144–155° C. |
| 49 | 1,3,5-Trimethylperhydrocyclopenta[b]pyrrole | (structure with CF₃, F, N–CF₃) | 145–156° C. |

TABLE 1-continued

| Example No. | Starting material | Perfluoro compound | B.P. (°C./760 mmHg) |
|---|---|---|---|
| 50 | 1,3,6-Trimethylperhydrocyclopenta[b]pyrrole | 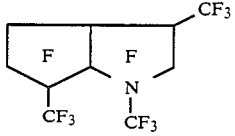 | 145–156° C. |
| 51 | 1,3,6a-Trimethylperhydrocyclopenta[b]pyrrole | 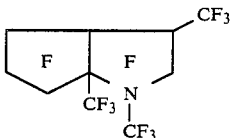 | 144–155° C. |
| 52 | 1,3a,4-Trimethylperhydrocyclopenta[b]pyrrole | 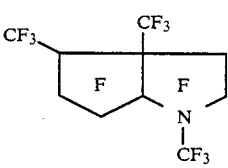 | 145–156° C. |
| 53 | 1,3a,5-Trimethylperhydrocyclopenta[b]pyrrole | 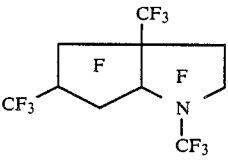 | 144–155° C. |
| 54 | 1,3a-6-Trimethylperhydrocyclopenta[b]pyrrole | 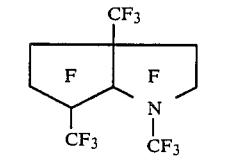 | 145–156° C. |
| 55 | 1,3a,6a-Trimethylperhydrocyclopenta[b]pyrrole | 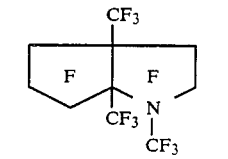 | 144–156° C. |
| 56 | 1,4,5-Trimethylperhydrocyclopenta[b]pyrrole | 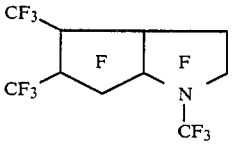 | 144–155° C. |
| 57 | 1,4,6-Trimethylperhydrocyclopenta[b]pyrrole | 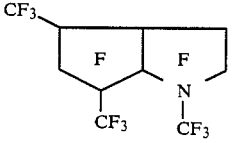 | 145–155° C. |
| 58 | 1,4,6a-Trimethylperhydrocyclopenta[b]pyrrole | 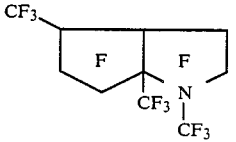 | 145–155° C. |
| 59 | 1,5,6-Trimethylperhydrocylcopenta[b]pyrrole | 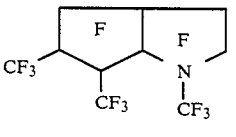 | 144–155° C. |

TABLE 1-continued

| Example No. | Starting material | Perfluoro compound | B.P. (°C./760 mmHg) |
|---|---|---|---|
| 60 | 1,5,6a-Trimethylperhydrocyclopenta[b]pyrrole | (structure with CF₃, F, CF₃, N-CF₃) | 144–155° C. |
| 61 | 1,6,6a-Trimethylperhydrocyclopenta[b]pyrrole | (structure with F, F, CF₃, CF₃, N-CF₃) | 145–156° C. |
| 62 | 1,2,2-Trimethylperhydrocyclopenta[b]pyrrole | (structure with F, F, CF₃, CF₃, N-CF₃) | 144–155° C. |
| 63 | 1,3,3-Trimethylperhydrocyclopenta[b]pyrrole | (structure with F, F, CF₃, CF₃, N-CF₃) | 144–156° C. |
| 64 | 1,4,4-Trimethylperhydrocyclopenta[b]pyrrole | (structure with CF₃, CF₃, F, F, N-CF₃) | 145–155° C. |
| 65 | 1,5,5-Trimethylperhydrocyclopenta[b]pyrrole | (structure with CF₃, CF₃, F, F, N-CF₃) | 144–155° C. |
| 66 | 1,6,6-Trimethylperhydrocyclopenta[b]pyrrole | (structure with F, F, CF₃, CF₃, N-CF₃) | 145–156° C. |
| 67 | 1,2-Dimethylperhydrocyclopenta[b]pyrrole | (structure with F, F, CF₃, N-CF₃) | 125–135° C. |
| 68 | 1,3-Dimethylperhydrocyclopenta[b]pyrrole | (structure with F, F, CF₃, N-CF₃) | 125–135° C. |
| 69 | 1,3a-Dimethylperhydrocyclopenta[b]pyrrole | (structure with CF₃, F, F, N-CF₃) | 125–135° C. |

TABLE 1-continued

| Example No. | Starting material | Perfluoro compound | B.P. (°C./760 mmHg) |
|---|---|---|---|
| 70 | 1,4-Dimethylperhydrocyclopenta[b]pyrrole | (structure with CF₃, F, F, N-CF₃) | 124-135° C. |
| 71 | 1,5-Dimethylperhydrocyclopenta[b]pyrrole | (structure with CF₃, F, F, N-CF₃) | 124-135° C. |
| 72 | 1,6-Dimethylperhydrocyclopenta[b]pyrrole | (structure with F, F, CF₃, N-CF₃) | 125-135° C. |
| 73 | 1,6a-Dimethylperhydrocyclopenta[b]pyrrole | (structure with F, F, CF₃, N-CF₃) | 125-135° C. |
| 74 | 1,2-Dimethylperhydrocyclopenta[c]pyrrole | (structure with F, F, N-CF₃, CF₃) | 125-135° C. |
| 75 | 2,3a-Dimethylperhydrocyclopenta[c]pyrrole | (structure with F, F, N-CF₃, CF₃) | 125-135° C. |
| 76 | 2,4-Dimethylperhydrocyclopenta[c]pyrrole | (structure with F, F, N-CF₃, CF₃) | 124-135° C. |
| 77 | 2,5-Dimethylperhydrocylcopenta[c]pyrrole | (structure with CF₃, F, F, N-CF₃) | 124-135° C. |
| 78 | 1,1,2-Trimethylperhydrocyclopenta[c]pyrrole | (structure with CF₃, CF₃, F, F, N-CF₃) | 145-155° C. |
| 79 | 2,4,4-Trimethylperhydrocyclopenta[c]pyrrole | (structure with CF₃, CF₃, F, F, N-CF₃) | 145-155° C. |
| 80 | 2,5,5-Trimethylperhydrocyclopenta[c]pyrrole | (structure with CF₃, CF₃, F, F, N-CF₃) | 144-155° C. |

TABLE 1-continued

| Example No. | Starting material | Perfluoro compound | B.P. (°C./760 mmHg) |
|---|---|---|---|
| 81 | 1,2,6a-Trimethylperhydrocyclopenta[c]pyrrole | bicyclic structure with CF3 (top-left quaternary), CF3 (top-right), F, F, N—CF3 | 144–156° C. |
| 82 | 1,2,6-Trimethylperhydrocyclopenta[c]pyrrole | bicyclic structure with CF3 (upper-left ring position), CF3 (top-right), F, F, N—CF3 | 144–155° C. |
| 83 | 1,2,5-Trimethylperhydrocyclopenta[c]pyrrole | bicyclic structure with CF3 (top), CF3— (left ring position), F, F, N—CF3 | 145–155° C. |
| 84 | 1,2,4-Trimethylperhydrocyclopenta[c]pyrrole | bicyclic structure with CF3 (top), F, F, N—CF3, CF3 (bottom-left) | 145–155° C. |
| 85 | 1,2,3a-Trimethylperhydrocyclopenta[c]pyrrole | bicyclic structure with CF3 (top), F, F, N—CF3, CF3 (bottom ring-junction) | 145–155° C. |
| 86 | 1,2,3-Trimethylperhydrocylcopenta[c]pyrrole | bicyclic structure with CF3 (top), F, F, N—CF3, CF3 (bottom-right) | 144–155° C. |
| 87 | 2,3a,4-Trimethylperhydrocyclopenta[c]pyrrole | bicyclic structure with CF3 (upper-left), CF3 (top ring-junction), F, F, N—CF3 | 144–155° C. |
| 88 | 2,3a,5-Trimethylperhydrocyclopenta[c]pyrrole | bicyclic structure with CF3 (top ring-junction), CF3— (left), F, F, N—CF3 | 145–155° C. |
| 89 | 2,3a,6-Trimethylperhydrocyclopenta[c]pyrrole | bicyclic structure with CF3 (top ring-junction), F, F, N—CF3, CF3 (bottom-left) | 145–155° C. |
| 90 | 2,3a,6a-Trimethylperhydrocyclopenta[c]pyrrole | bicyclic structure with CF3 (top ring-junction), F, F, N—CF3, CF3 (bottom ring-junction) | 145–155° C. |

TABLE 1-continued

| Example No. | Starting material | Perfluoro compound | B.P. (°C./760 mmHg) |
|---|---|---|---|
| 91 | 2,4,5-Trimethylperhydrocyclopenta[c]pyrrole | (structure with CF₃, CF₃, F, F, N—CF₃) | 144–155° C. |
| 92 | 2,4,6-Trimethylperhydrocyclopenta[c]pyrrole | (structure with CF₃, F, F, N—CF₃, CF₃) | 145–155° C. |
| 93 | 1-Ethyl-2-methylperhydrocyclopenta[c]pyrrole | (structure with CF₂CF₃, F, F, N—CF₃) | 145–155° C. |
| 94 | 3a-Ethyl-2-methylperhydrocyclopenta[c]pyrrole | (structure with CF₂CF₃, F, F, N—CF₃) | 145–155° C. |
| 95 | 4-Ethyl-2-methylperhydrocyclopenta[c]pyrrole | (structure with CF₂CF₃, F, F, N—CF₃) | 145–156° C. |
| 96 | 5-Ethyl-2-methylperhydrocyclopenta[c]pyrrole | (structure with CF₃CF₂, F, F, N—CF₃) | 145–156° C. |
| 97 | 1,4a-Dimethylperhydropyridine | (structure with CF₃, F, F, N—CF₃) | 145–155° C. |

The perfluoro compound emulsion of the present invention is illustrated in detail below by the Examples and Experimental Examples using as examples perfluoro-N-methyldecahydroquinoline [hereinafter referred to as compound (II)] and perfluoro-N-methyldecahydroisoquinoline [hereinafter referred to as compound (III)], each represented by the following formula (II) and (III) respectively.

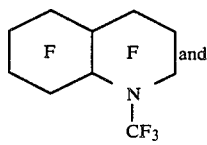

(II)

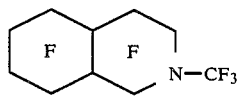

(III)

But this invention should not be constructed thereto.

EMULSION PREPARATION EXAMPLE 1

In 8.5 l of lactated Ringer's solution, were added 400 g of egg yolk phospholipid and 4 g of sodium palmitate, and the resulting mixture was stirred in a mixer to form an emulsified liquid. Into this liquid was added 2.5 Kg of compound (III), and the mixture was stirred further in a mixer vigorously to form a crude emulsion. The resulting crude emulsion was charged in the liquor tank of a jet emulsifier (made by Manton-Gaulin Co.) and was circulated in the emulsifier, while maintaining the liquor temperature at 50±5° C., to effect emulsification. The resulting emulsion contained 27.3% (W/V) of compound (III). The particle diameters were 0.05–0.25μ as determined by the centrifugal sedimentation method. When the emulsion was enclosed in a vial for injection and subjected to thermal sterilization in a rotary sterilizer there was no remarkable growth in particle size.

EMULSION PREPARATION EXAMPLE 2

The procedures of Emulsion Preparation Example 1 were repeated except that compound (II) was used in place of compound (III), to obtain an emulsion. The emulsion obtained had particle diameters of 0.05–0.25μ, and showed no remarkable growth in particle size even after being subjected to thermal sterilization.

EXPERIMENTAL EXAMPLE 1

Stability of an emulsion

Water was added to each of 20 g of compound (II) and (III), respectively, and 4 g of egg yolk phospholipid to make up the total to 200 ml. The resulting mixture was emulsified by means of a Manton-Gaulin type emulsifier at a pressure of 200–600 kg/cm$^2$ under nitrogen gas stream while maintaining the liquor temperature at 40°–45° C. Each of the resulting emulsion was filtered through a membrane filter having a pore size of 0.65μ, subdivided and put into 20 ml vial. Afte replacing the atmosphere with nitrogen, the emulsion was heat treated at 100° C. for 30 minutes, then stored at an ambient temperature of 4° C. and examined for its stability. The particle size of the emulsion was measured by the centrifugal sedimentation method proposed by Yokoyama et al [Chem. Pharm. Bull. 22 (12), 2966 (1974)]. From the data thus obtained, the average particle size and the particle size distribution were calculated by use of a microcomputer.

In Table 2-1 and Table 2-2 were shown the particle size distribution of the respective emulsion before and after heat treatment as well as after stored at 4° C. and at room temperature (15°–28° C.) following the heat treatment. As is apparent from these results, the emulsion of the present invention was very stable to heat treatment, and there was observed no effect of heat treatment on the average particle size. Also, when stored at 4° C. after heat treatment, no growth in average particle size was observed even after 5 months.

TABLE 2-1

Stability of compound (II) emulsion

| | Average particle diameter μ | Particle size distribution % by weight | | |
|---|---|---|---|---|
| | | <0.1μ | 0.1–0.2μ | 0.2–0.3μ | >0.3μ |
| Before heat treatment | 0.112 | 42.1 | 50.6 | 7.3 | 0 |
| Immediately after heat treatment | 0.115 | 38.2 | 57.8 | 4.0 | 0 |
| After 2 weeks, 4° C. | 0.110 | 41.3 | 57.6 | 1.1 | 0 |
| room temp. | 0.112 | 39.7 | 57.6 | 2.6 | 0 |
| After 2 weeks, 4° C. | 0.113 | 39.4 | 57.9 | 2.7 | 0 |
| room temp. | 0.123 | 32.3 | 61.7 | 6.1 | 0 |
| After 5 months, 4° C. | 0.110 | 41.3 | 56.6 | 2.1 | 0 |

TABLE 2-2

Stability of compound (III) emulsion

| | Average particle diameter μ | Particle size distribution % by weight | | |
|---|---|---|---|---|
| | | <0.1μ | 0.1–0.2μ | 0.2–0.3μ | >0.3μ |
| Before heat treatment | 0.122 | 39.0 | 50.2 | 10.8 | 0 |
| Immediately after heat treatment | 0.122 | 35.5 | 59.5 | 6.1 | 0 |
| After 2 weeks 4° C. | 0.123 | 38.1 | 60.7 | 1.2 | 0 |
| room temp. | 0.128 | 32.3 | 64.6 | 3.1 | 0 |
| After 4 weeks 4° C. | 0.120 | 37.5 | 61.2 | 1.3 | 0 |
| room temp. | 0.129 | 33.3 | 61.5 | 5.2 | 0 |
| After 5 months 4° C. | 0.123 | 38.0 | 59.7 | 2.3 | 0 |

EXPERIMENTAL EXAMPLE 2

Acute toxicity test

The acute toxicity tests were performed by using the emulsion of the present invention which had been prepared by diluting the respective emulsion of compound (II) and compound (III) shown in Table 3 with the electrolytes solution shown in the table in a ratio of 9:1 to make the resulting emulsion physiologically isotonic. Wister strain male rats (weighing 100–120 g) were used as test animals. The rats were intravenously injected with the emulsion, and observed for a period of one week after administration.

As the result, no death was observed in all the animals at a dose of 100 ml/kg body weight of both emulsion containing compound (II) or compound (III), indicating that both were of very low toxicity.

TABLE 3

| Composition | | | Emulsion of this invention |
|---|---|---|---|
| Emulsion component (9 vol.) | Perfluoro carbon | Compound (II) or Compound (III) | 30% (W/V) |
| | Emulsifier | Pluronic F-68 | 3.4 |
| | | Yolk phospholipid | 0.6 |
| | | Potassium oleate | 0.004 |
| Electrolytes solution (1 vol.) | | NaCl | 6.00 |
| | | NaHCO$_3$ | 2.1 |
| | | KCl | 0.336 |
| | | Sodium lactate | — |
| | | MgCl$_2$.6H$_2$O | 0.427 |
| | | CaCl$_2$.6H$_2$O | 0.356 |
| | | D-glucose | 1.802 |
| | pH | | 8.0 |

*Polyoxyethylene-polyoxypropylene copolymer

EXPERIMENTAL EXAMPLE 3

Distribution among internal organs of the perfluoro compounds after administration Wister strain male rats weighing 120–130 g were used to be administered through tail vein with the emulsion of compound (II) prepared in Emulsion Preparation Example 2 [at a dose of 4 g/kg as compound (II)]. The contents of compound (II) taken into the liver, spleen and fat tissue were determined by gas chromatography during the period of 3 months after administration.

The contents of compound (II) taken into each internal organ 1, 2 and 4 weeks and 3 months after administration were shown in Table 4. These compounds were mostly taken into the reticuloendothelial system tissue in the early stage after administration, and then diminished rapidly. The total amount of compound (II) remaining in these organs three months after administration was 0.66% of the amount administered. No adverse effect on each of the organs, liver and spleen, was observed.

From the results of above determinations the half life of compound (II) was calculated at 9.36 days.

TABLE 4

| Organ | Time elapsed after administration | Compound (II) mg/g cell | Residual proportion(%) |
|---|---|---|---|
| Liver | 1 week | 9.08 (1.23) | 19.58 (2.68) |
|  | 2 weeks | 5.00 (1.35) | 13.67 (4.43) |
|  | 4 weeks | 0.80 (0.30) | 2.79 (1.13) |
|  | 3 months | 0.06 (0.01) | 0.20 (0.04) |
| Spleen | 1 week | 67.46 (15.35) | 12.17 (2.34) |
|  | 2 weeks | 43.55 (3.03) | 10.41 (0.56) |
|  | 4 weeks | 20.44 (7.86) | 4.07 (0.86) |
|  | 3 months | 2.20 (0.61) | 0.46 (0.10) |
| Fat tissue | 1 week | 1.94 (0.59) | 4.53 (1.30) |
|  | 2 weeks | 2.72 (0.43) | 7.93 (1.14) |
|  | 4 weeks | 1.21 (0.05) | 4.89 (0.46) |
|  | 3 months | 0.17 (0.04) | 1.08 (0.24) |

EXPERIMENTAL EXAMPLE 4

Anatomical consideration and change of relative weight based on body weight

Wister strain male rats weighing 120—130 g were used to be administered with 4 g/Kg of the perfluorocarbon compound emulsion each prepared in Emulsion Preparation Examples 1 and 2. During the period of three months after administration, the rats were dissected for observation of internal organs, and the weights of the organs were measured to determine the relative organ weight (g) based on the body weight (kg).

The rats were dissected 1, 2 and 4 weeks and 3 months after the administration of emulsion, and the main organs of lung, liver and spleen were visually inspected. There was observed no effect exerted on the organs with either of the compounds because of their very rapid excretion. The changes of the relative weights of liver and spleen based on the body weight were shown in FIG. 1 and FIG. 2, respectively. The differences between these values and those of the reference test animals (administered with physiological saline solution) disappeared completely after about 3 months.

What is claimed is:

1. A perfluoro compound represented by the formula,

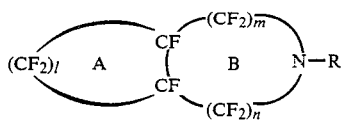

wherein R denotes a lower perfluoroalkyl group, l is an integer of 3 or 4, n+m is an integer of 2 or 3, provided that n may be zero, and at least one of the ring fluorines of ring A or ring B is optionally replaced by a lower perfluoroalkyl group.

2. The perfluoro compound of claim 1, wherein the condensed ring skeleton A+B is perhydro-quinoline, perhydro isoquinoline, perhydro-indole, perhydro-isoindole, perhydro cyclopenta[b]pyrrole, perhydro-cyclopenta[c]pyrrole, perhydro pyridine, and perhydro-isopyridine, all of which has been perfluorinated.

3. A compound according to claim 1 wherein R stands for trifluoromethyl.

4. A compound according to claim 2 wherein A and B represent perhydro-quinoline which has been perfluorinated.

5. A compound according to claim 2 wherein A and B represent perhydro-isoquinoline which has been perfluorinated.

6. A compound according to claim 2 wherein A and B represent perhydro-indole which has been perfluorinated.

7. A compound according to claim 2 wherein A and B represent perhydro-isoindole which has been perfluorinated.

8. A compound according to claim 2 wherein A and B represent perhydro-cyclopenta(b)-pyrrole which has been perfluorinated.

9. A compound according to claim 2 where A and B represent perhydro-cyclopentapyrrole which has been perfluorinated.

10. A compound according to claim 2 wherein A and B represent perhydro-cyclopentapyridine which has been perfluorinated.

11. A compound according to claim 2 wherein A and B represent perhydro-cyclopenta(c)pyridine which has been perfluorinated.

* * * * *